US008568475B2

(12) United States Patent  
Nguyen et al.

(10) Patent No.: US 8,568,475 B2  
(45) Date of Patent: Oct. 29, 2013

(54) SPIRALED COMMISSURE ATTACHMENT FOR PROSTHETIC VALVE

(75) Inventors: Son V. Nguyen, Irvine, CA (US); Netanel Benichou, D.N. Hof Hacarmel (IL)

(73) Assignee: Edwards Lifesciences Corporation, Irvine, CA (US)

(*) Notice: Subject to any disclaimer, the term of this patent is extended or adjusted under 35 U.S.C. 154(b) by 61 days.

(21) Appl. No.: 13/253,698

(22) Filed: Oct. 5, 2011

(65) Prior Publication Data

US 2012/0089223 A1  Apr. 12, 2012

Related U.S. Application Data

(60) Provisional application No. 61/390,107, filed on Oct. 5, 2010.

(51) Int. Cl.
*A61F 2/24* (2006.01)
(52) U.S. Cl.
USPC .................................. 623/2.12; 623/2.17
(58) Field of Classification Search
USPC ...................... 623/2.1, 2.11–2.19
See application file for complete search history.

(56) References Cited

U.S. PATENT DOCUMENTS

| | | | |
|---|---|---|---|
| 3,409,013 A | 11/1968 | Berry | |
| 3,467,102 A | 9/1969 | Fogarty et al. | |
| 3,548,417 A | 12/1970 | Kisher | |
| 3,587,115 A | 6/1971 | Shiley | |
| 3,657,744 A | 4/1972 | Ersek | |
| 3,671,979 A | 6/1972 | Moulopoulos | |
| 3,714,671 A | 2/1973 | Edwards et al. | |
| 3,755,823 A | 9/1973 | Hancock | |
| 4,035,849 A | 7/1977 | Angell et al. | |
| 4,056,854 A | 11/1977 | Boretos et al. | |
| 4,106,129 A | 8/1978 | Carpentier et al. | |
| 4,222,126 A | 9/1980 | Boretos et al. | |
| 4,265,694 A | 5/1981 | Boretos et al. | |
| 4,297,749 A | 11/1981 | Davis et al. | |
| 4,339,831 A | 7/1982 | Johnson | |
| 4,343,048 A | 8/1982 | Ross et al. | |

(Continued)

FOREIGN PATENT DOCUMENTS

| | | |
|---|---|---|
| DE | 2246526 A1 | 3/1973 |
| DE | 19532846 A1 | 3/1997 |

(Continued)

OTHER PUBLICATIONS

Andersen, et al., "Transluminal implantation of artificial heart valves. Description of a new expandable aortic valve and initial results with implantation by catheter technique in closed chest pigs." European Heart Journal (1992), 13, 704-708.

(Continued)

*Primary Examiner* — David Isabella  
*Assistant Examiner* — Randy Shay  
(74) *Attorney, Agent, or Firm* — David L. Hauser

(57) ABSTRACT

An implantable prosthetic valve, according to one embodiment, comprises a radially collapsible and expandable frame and a leaflet structure supported within the frame. The leaflet structure can comprise a plurality of leaflets paired together at commissures. In one embodiment, the commissures can comprise leaflet tabs rolled into spirals around non-rigid reinforcing inserts. In another embodiment, the commissures can comprise a reinforcing sheet folded around leaflet tabs.

19 Claims, 11 Drawing Sheets

(56) References Cited

U.S. PATENT DOCUMENTS

| | | |
|---|---|---|
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,796,629 A | 1/1989 | Grayzel |
| 4,797,901 A | 1/1989 | Goerne et al. |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,571,175 A | 11/1996 | Vanney et al. |
| 5,591,185 A | 1/1997 | Kilmer et al. |
| 5,607,464 A | 3/1997 | Trescony et al. |
| 5,609,626 A | 3/1997 | Quijano et al. |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,925,063 A | 7/1999 | Khosravi |
| 5,957,949 A | 9/1999 | Leonhardt et al. |
| 6,027,525 A | 2/2000 | Suh et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,299,637 B1 | 10/2001 | Shaolian et al. |
| 6,302,906 B1 | 10/2001 | Goicoechea et al. |
| 6,350,277 B1 | 2/2002 | Kocur |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,569,196 B1 | 5/2003 | Vesely |
| 6,605,112 B1 | 8/2003 | Moll et al. |
| 6,730,118 B2 | 5/2004 | Spenser et al. |
| 6,733,525 B2 | 5/2004 | Yang et al. |
| 6,830,584 B1 | 12/2004 | Seguin |
| 6,893,460 B2 | 5/2005 | Spenser et al. |
| 6,908,481 B2 | 6/2005 | Cribier |
| 7,018,406 B2 | 3/2006 | Seguin et al. |
| 7,276,078 B2 | 10/2007 | Spenser et al. |
| 7,276,084 B2 | 10/2007 | Yang et al. |
| 7,374,571 B2 | 5/2008 | Pease et al. |
| 7,393,360 B2 | 7/2008 | Spenser et al. |
| 7,462,191 B2 | 12/2008 | Spenser et al. |
| 2001/0021872 A1 | 9/2001 | Bailey et al. |
| 2002/0032481 A1 | 3/2002 | Gabbay |
| 2002/0173842 A1 | 11/2002 | Buchanan |
| 2003/0050694 A1 | 3/2003 | Yang et al. |
| 2003/0100939 A1 | 5/2003 | Yodfat et al. |
| 2003/0212454 A1 | 11/2003 | Scott et al. |
| 2004/0039436 A1 | 2/2004 | Spenser et al. |
| 2004/0186565 A1 | 9/2004 | Schreck |
| 2004/0260389 A1 | 12/2004 | Case et al. |
| 2005/0234546 A1 | 10/2005 | Nugent et al. |
| 2006/0025857 A1 | 2/2006 | Bergheim et al. |
| 2006/0149350 A1 | 7/2006 | Patel et al. |
| 2006/0229719 A1 | 10/2006 | Marquez et al. |
| 2006/0259137 A1 | 11/2006 | Artof et al. |
| 2008/0154355 A1 | 6/2008 | Benichou et al. |
| 2010/0023120 A1* | 1/2010 | Holecek et al. ............ 623/2.19 |
| 2012/0059487 A1* | 3/2012 | Cunanan et al. ........... 623/23.72 |

FOREIGN PATENT DOCUMENTS

| | | |
|---|---|---|
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 A1 | 3/1984 |
| EP | 0144167 A2 | 6/1985 |
| EP | 0592410 A1 | 4/1994 |
| EP | 0597967 A1 | 5/1994 |
| EP | 0850607 A1 | 7/1998 |
| EP | 1057460 A1 | 12/2000 |
| EP | 1088529 A2 | 4/2001 |
| EP | 1570809 A1 | 9/2005 |
| FR | 2788217 A1 | 7/2000 |
| GB | 2056023 A | 3/1981 |
| SU | 158988 | 11/1963 |
| SU | 1271508 A1 | 11/1986 |
| SU | 1371700 A1 | 2/1988 |
| SU | 1457921 A1 | 2/1989 |
| WO | 91/17720 A1 | 11/1991 |
| WO | 92/17118 A1 | 10/1992 |

(56) References Cited

FOREIGN PATENT DOCUMENTS

| | | |
|---|---|---|
| WO | 93/01768 A1 | 2/1993 |
| WO | 97/24080 A1 | 7/1997 |
| WO | 98/29057 A1 | 7/1998 |
| WO | 99/33414 A1 | 7/1999 |
| WO | 99/40964 A1 | 8/1999 |
| WO | 99/47075 A1 | 9/1999 |
| WO | 00/18333 A1 | 4/2000 |
| WO | 00/41652 A1 | 7/2000 |
| WO | 00/47139 A1 | 8/2000 |
| WO | 01/35878 A2 | 5/2001 |
| WO | 01/49213 A2 | 7/2001 |
| WO | 01/54624 A1 | 8/2001 |
| WO | 01/54625 A1 | 8/2001 |
| WO | 01/62189 A1 | 8/2001 |
| WO | 01/64137 A1 | 9/2001 |
| WO | 01/76510 A2 | 10/2001 |
| WO | 02/22054 A1 | 3/2002 |
| WO | 02/36048 A1 | 5/2002 |
| WO | 02/41789 A2 | 5/2002 |
| WO | 02/43620 A1 | 6/2002 |
| WO | 02/47575 A2 | 6/2002 |
| WO | 02/49540 A2 | 6/2002 |
| WO | 03/047468 A1 | 6/2003 |
| WO | 2005/087140 A1 | 9/2005 |
| WO | 2006/014233 A2 | 2/2006 |
| WO | 2006/034008 A2 | 3/2006 |
| WO | 2008/005405 A2 | 1/2008 |
| WO | 2008/035337 A2 | 3/2008 |
| WO | 2008/147964 A1 | 12/2008 |
| WO | 2008/150529 A1 | 12/2008 |

OTHER PUBLICATIONS

Andersen, Henning Rud, "History of Percutaneous Aortic Valve Prosthesis," Herz 34 2009 Nr. 5, Urban & Vogel, pp. 343-346, Skejby University Hospital Department of Cardiology, Aarhus, Denmark.

Almagor, M.D., Yaron, et al., "Balloon Expandable Stent Implantation in Stenotic Right Heart Valved Conduits," Journal of the American College of Cardiology, vol. 16, No. 6, pp. 1310-1314, Nov. 1, 1990; ISSN 0735-1097.

Sabbah, Ph.D., Hani N., et al., "Mechanical Factors in the Degeneration of Porcine Bioprosthetic Valves: An Overview," Journal of Cardiac Surgery, vol. 4, No. 4, pp. 302-309, Dec. 1989; ISSN 0886-0440.

Serruys, P.W., et al., "Stenting of Coronary Arteries. Are we the Sorcerer's Apprentice?," European Heart Journal (1989) 10, 774-782, pp. 37-45, Jun. 13, 1989.

Kolata, Gina, "Device That Opens Clogged Arteries Gets a Failing Grade in a New Study," nytimes.com, http://www.nytimes.com/1991/01/03/health/device-that-opens-clogged-arteries-gets-a-faili . . . , Jul. 29, 2009, 2 pages.

Urban, M.D., Philip, "Coronary Artery Stenting," Editions Médecine et Hygiène, Genève, 1991, pp. 5-47.

Al-Khaja, N., et al., "Eleven Years' Experience with Carpentier-Edwards Biological Valves in Relation to Survival and Complication," European Journal of Cardiothoracic Surgery 3:305-311, Jun. 30, 2009.

Wheatley, M.D., David J., "Valve Prostheses," Rob & Smith's Operative Surgery, Fourth Edition, pp. 415-424, Butterworths 1986.

Benchimol, Alberto, et al., "Simultaneous Left Ventricular Echocardiography and Aortic Blood Velocity During Rapid Right Ventricular Pacing in Man," The American Journal of the Medical Sciences, Jan.-Feb. 1977 vol. 273, No. 1, pp. 55-62.

Watt, A.H., et al. "Intravenous Adenosine in the Treatment of Supraventricular Tachycardia; a Dose-Ranging Study and Interaction with Dipyridamole," British Journal of Clinical Pharmacology (1986), 21, 227-230.

Uchida, Barry T., et al., "Modifications of Gianturco Expandable Wire Stents," AJR:150, May 1988, Dec. 3, 1987, pp. 1185-1187.

Selby, M.D., J. Bayne, "Experience with New Retrieval Forceps for Foreign Body Removal in the Vascular, Urinary, and Biliary Systems," Radiology 1990; 176:535-538.

Inoune, M.D., Kanji, et al., "Clinical Application of Transvenous Mitral Commissurotomy by a New Balloon Catheter," The Journal of Thoracic and Cardiovascular Surgery 87:394-402, 1984.

AL Ziabag, Muayed, et al., "Percutaneous Balloon Valvotomy in Tricuspid Stenosis," British Heart Journal, Jan. 1987, vol. 57, No. 1, pp. 51-53.

Lawrence, Jr., M.D., David D., "Percutaneous Endovascular Graft: Experimental Evaluation," Radiology 1897; 163: 357-360.

Dotter, M.D., Charles T., "Transluminal Treatment of Arteriosclerotic Obstruction," University of Oregon's Minthorn Memorial Laboratory for Cardiovascular Research through Radiology, Circulation, vol. XXX, Nov. 1964, pp. 654-670.

Sigwart, Ulrich, "An Overview of Intravascular Stents: Old and New," Chapter 48, Textbook of Interventional Cardiology, 2nd Edition, W.B. Saunders Company, Philadelphia, PA, © 1994, 1990, pp. 803-815.

Rashkind, M.D., William J., "Historical Aspects of Interventional Cardiology: Past, Present, Future," Texas Heart Institute Journal, Interventional Cardiology, pp. 363-367.

Rosch, M.D., Josef, "The Birth, Early Years and Future of Interventional Radiology," J Vasc Intery Radiol 2003; 14:841-853.

Pavcnik, M.D., Ph.D., Dusan, et al. "Development and Initial Experimental Evaluation of a Prosthetic Aortic Valve for Transcatheter Placement," Cardiovascular Radiology 1992; 183:151-154.

Ross, F.R.C.S., D.N., "Aortic Valve Surgery," Guy's Hospital, London, pp. 192-197, approximately 1968.

Rashkind, M.D., William J., "Creationof an Atrial Septal Defect Withoput Thoracotomy," The Journal of the American Medical Association, vol. 196, No. 11, Jun. 13, 1966, pp. 173-174.

Porstmann, W., et al., "Der Verschluβ des Ductus Arteriosus Persistens ohne Thorakotomie," Thoraxchirurgie Vaskuläre Chirurgie, Band 15, Heft 2, Stuttgart, im Apr. 1967, pp. 199-203.

* cited by examiner

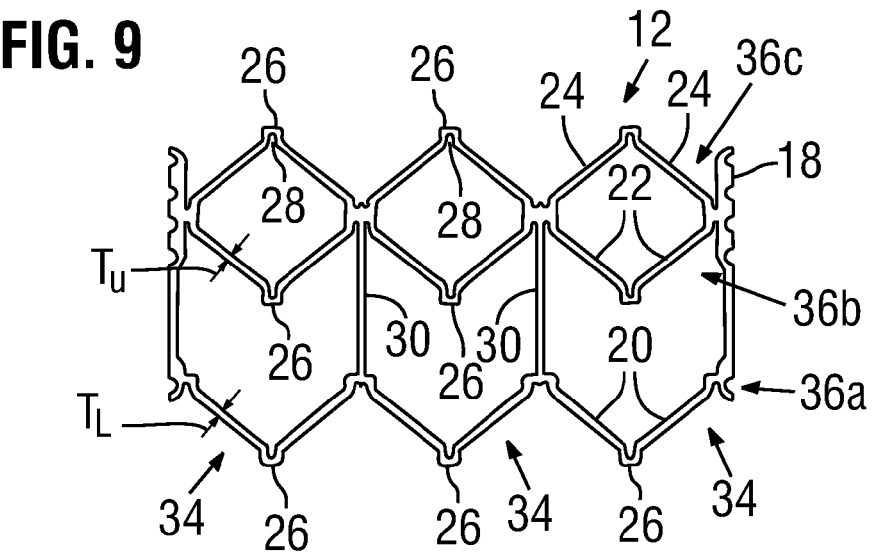
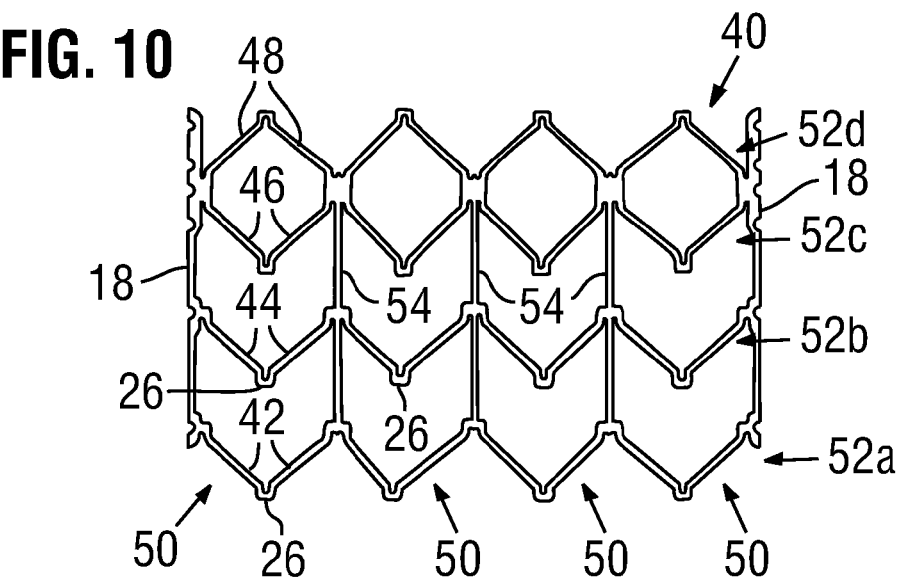
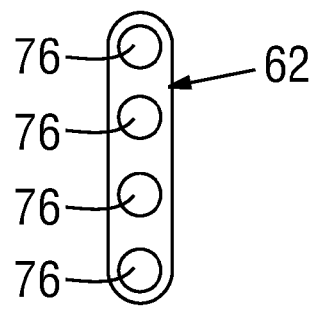

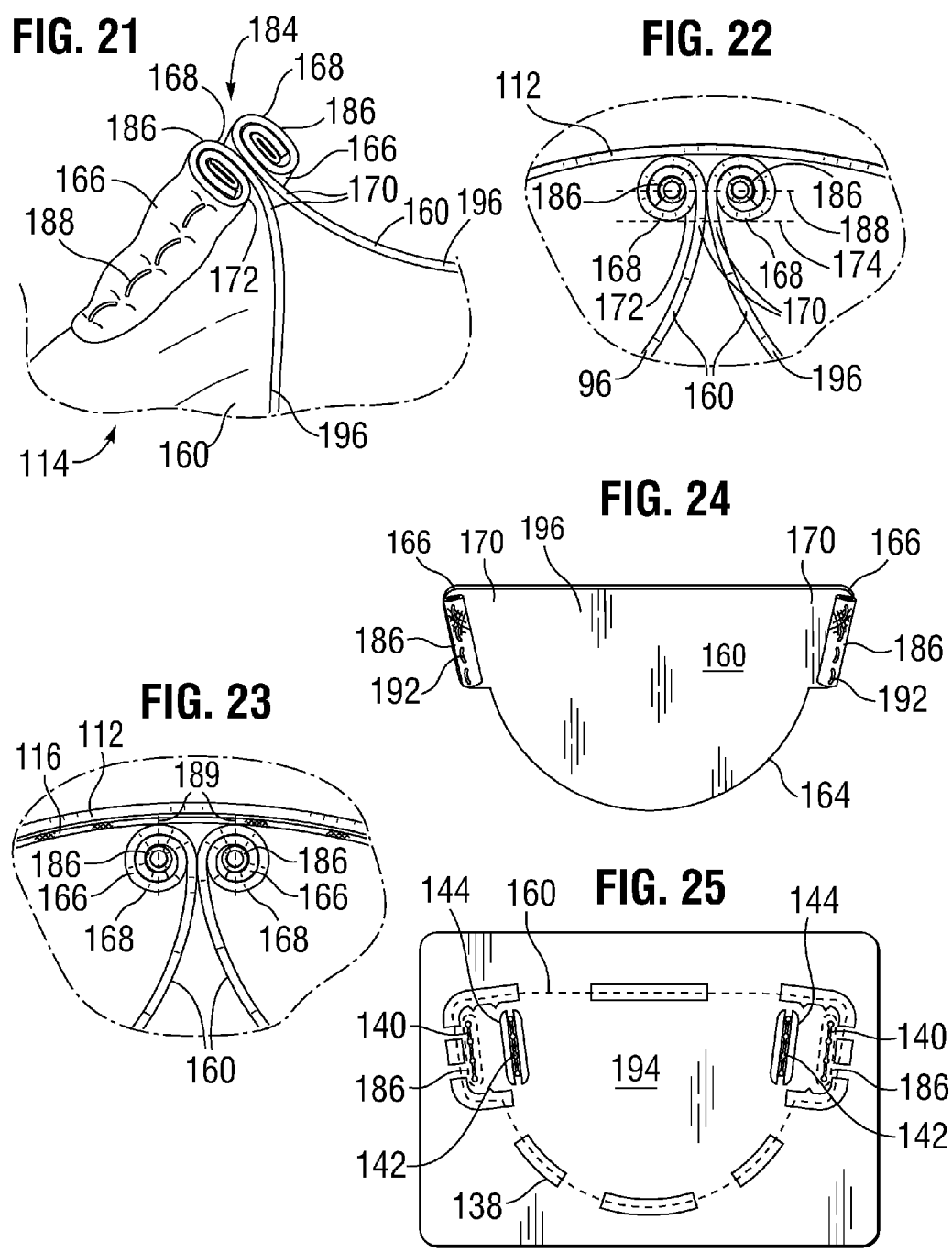

SPIRALED COMMISSURE ATTACHMENT FOR PROSTHETIC VALVE

CROSS REFERENCE TO RELATED APPLICATION

This application claims the benefit of U.S. Provisional Patent Application Ser. No. 61/390,107, filed Oct. 5, 2010, which is incorporated herein by reference.

FIELD

The present disclosure relates to implantable prosthetic devices and, more particularly, to prosthetic valves for implantation into body ducts, such as native heart valve annuluses.

BACKGROUND

The human heart can suffer from various valvular diseases. These valvular diseases can result in significant malfunctioning of the heart and ultimately require replacement of the native valve with an artificial valve. There are a number of known artificial valves and a number of known methods of implanting these artificial valves in humans.

Various surgical techniques may be used to replace or repair a diseased or damaged valve. Due to stenosis and other heart valve diseases, thousands of patients undergo surgery each year wherein the defective native heart valve is replaced by a prosthetic valve. Another less drastic method for treating defective valves is through repair or reconstruction, which is typically used on minimally calcified valves. The problem with surgical therapy is the significant risk it imposes on these chronically ill patients with high morbidity and mortality rates associated with surgical repair.

When the native valve is replaced, surgical implantation of the prosthetic valve typically requires an open-chest surgery during which the heart is stopped and patient placed on cardiopulmonary bypass (a so-called "heart-lung machine"). In one common surgical procedure, the diseased native valve leaflets are excised and a prosthetic valve is sutured to the surrounding tissue at the valve annulus. Because of the trauma associated with the procedure and the attendant duration of extracorporeal blood circulation, some patients do not survive the surgical procedure or die shortly thereafter. It is well known that the risk to the patient increases with the amount of time required on extracorporeal circulation. Due to these risks, a substantial number of patients with defective native valves are deemed inoperable because their condition is too frail to withstand the procedure. By some estimates, more than 50% of the subjects suffering from valve stenosis who are older than 80 years cannot be operated on for valve replacement.

Because of the drawbacks associated with conventional open-heart surgery, percutaneous and minimally-invasive surgical approaches are garnering intense attention. In one technique, a prosthetic valve is configured to be implanted in a much less invasive procedure by way of catheterization. For instance, U.S. Pat. Nos. 5,411,522 and 6,730,118, which are incorporated herein by reference, describe collapsible transcatheter heart valves that can be percutaneously introduced in a compressed state on a catheter and expanded in the desired position by balloon inflation or by utilization of a self-expanding frame or stent.

An important design parameter of a transcatheter heart valve is the diameter of the folded or crimped profile. The diameter of the crimped profile is important because it directly influences the physician's ability to advance the transcatheter heart valve through the femoral artery or vein. More particularly, a smaller profile allows for treatment of a wider population of patients, with enhanced safety.

SUMMARY

The present disclosure is directed toward methods and apparatuses relating to prosthetic valves, such as heart valves.

In one exemplary embodiment, an implantable prosthetic valve comprises a radially collapsible and expandable annular frame and a leaflet structure positioned within the frame. The leaflet structure comprises a plurality of leaflets each having two opposing side tabs. Each side tab is rolled into a spiral and each spiral is coupled to an adjacent spiral of an adjacent leaflet to form commissures of the leaflet structure. Each commissure is coupled to the frame. Each spiral can further include a non-rigid reinforcing insert positioned within the spiral such that sutures that secure the commissures intersect the reinforcing inserts.

In yet another exemplary embodiment, an implantable prosthetic valve comprises a radially collapsible and expandable annular frame and a valve structure positioned within the frame. The valve structure comprises a plurality of leaflets and a plurality of flexible reinforcing sheets. Each leaflet comprises two opposing side tabs, each side tab being coupled to an adjacent side tab of another leaflet and to one of the reinforcing sheets to form reinforced commissures of the valve structure. Each commissure is coupled to the frame. Each leaflet side tab comprises a medial portion and an end portion extending from the medial portion. For each side tab, the medial portion is in contact with the medial portion of the adjacent side tab and the end portion is folded back away from the adjacent side tab and adjacent to the medial portion. Each sheet comprises a middle portion extending circumferentially between the side tabs and the frame. First and second side portions of each sheet extend radially inwardly from respective opposing ends of the middle portion of the sheet and around the end portions of the respective side tabs. First and second end portions of each sheet extend radially outwardly from radially inner ends of the first and second side portions of the sheet, respectively. Each end portion of the sheet is sandwiched between the medial portion and the end portion of a respective side tab.

The foregoing and other features and advantages of the invention will become more apparent from the following detailed description, which proceeds with reference to the accompanying figures.

BRIEF DESCRIPTION OF THE DRAWINGS

FIG. 9 is a flattened view of 120-degree segment of the frame shown in FIG. 7.

FIG. 10 is a flattened view of 120-degree segment of the frame shown in FIG. 8.

FIG. 11 is a front view of a reinforcing bar that can be used to reinforce the connection of the valve leaflets to a frame in a prosthetic valve such as shown in FIG. 1.

FIG. 21 is an enlarged, perspective view of a pair of leaflets of the valve of FIG. 19, the leaflets having side tabs rolled into spirals and sutured together.

FIG. 22 is a top view of a commissure of the valve of FIG. 19, before the spirals are compressed by the sutures, showing an exemplary radial spacing between a suture line and a flex hinge line.

FIG. 23 is a top view of a commissure of an alternative valve embodiment, wherein the spirals are sutured to an annular skirt.

FIG. 24 shows an exemplary leaflet laid flat with reinforcing inserts sutured to opposing side tabs of the leaflet.

FIG. 25 shows an exemplary template that can be used to suture the reinforcing inserts to the side tabs of the leaflets.

DETAILED DESCRIPTION

Figure 1:
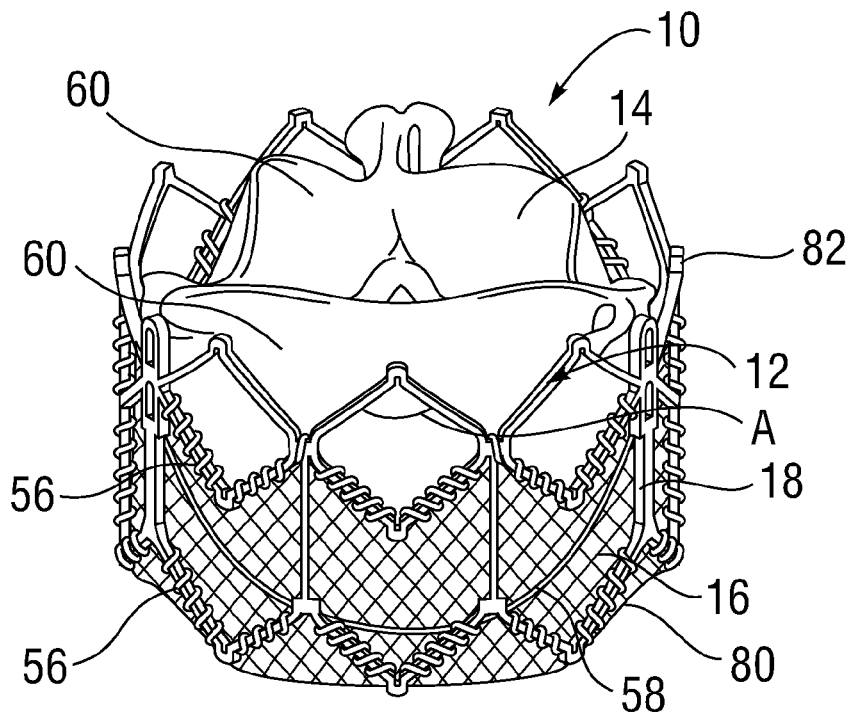
FIG. 1 is a perspective view of a representative embodiment of a prosthetic heart valve.
Figure 2:
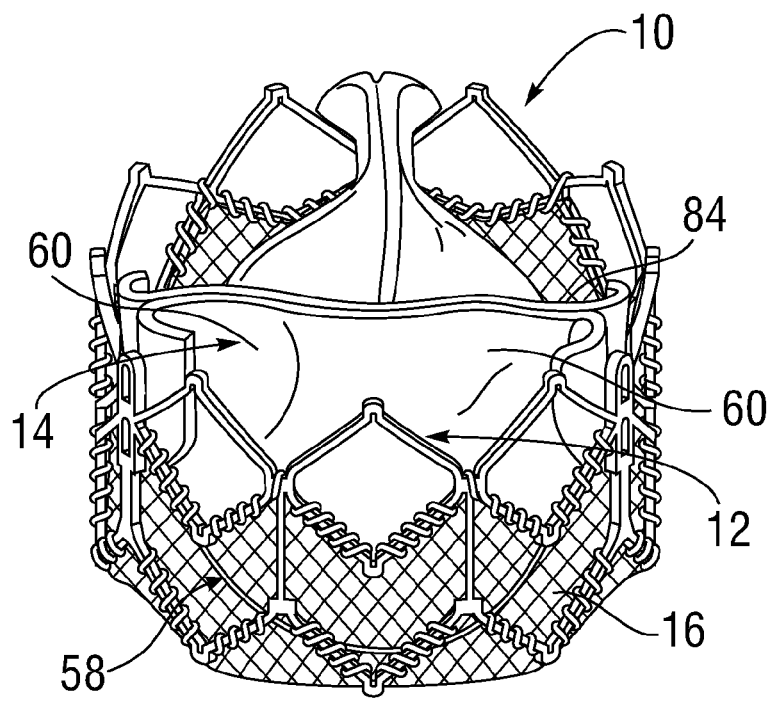
FIG. 2 is another perspective view illustrating the prosthetic valve of FIG. 1 in a closed position.
Figure 3:
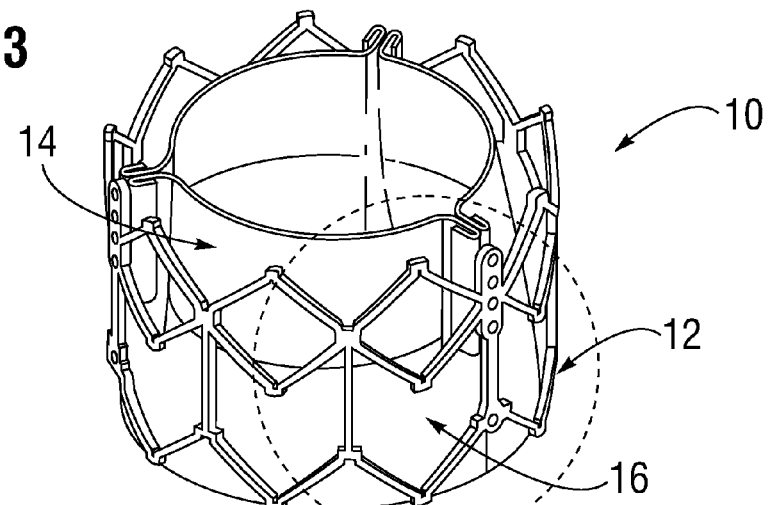
FIG. 3 is another perspective view of the prosthetic valve of FIG. 1.
Figure 4:
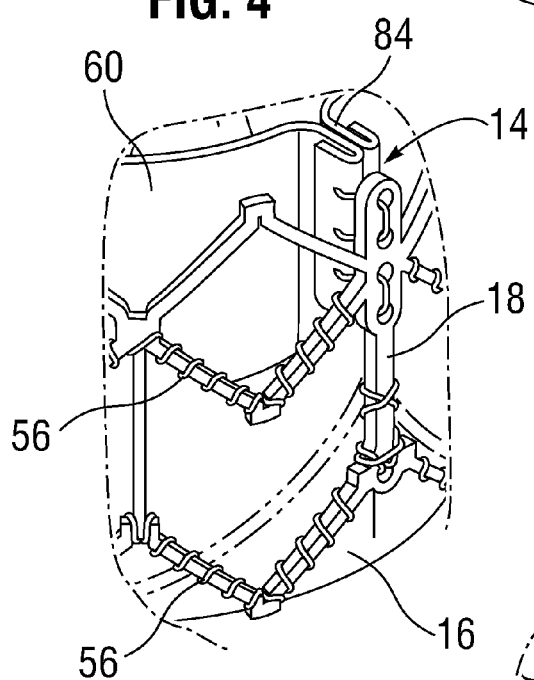
FIG. 4 is an enlarged view of a section of the valve shown in FIG. 3.

FIGS. 1 and 2 illustrate an implantable prosthetic valve 10, according to one embodiment. Prosthetic valve 10 in the illustrated embodiment generally comprises a frame, or stent, 12, a leaflet structure 14 supported by the frame, and a skirt 16 secured to the inner surface of the frame. Prosthetic valve 10 typically is implanted in the annulus of the native aortic valve but also can be adapted to be implanted in other native valves of the heart or in various other ducts or orifices of the body. Prosthetic valve 10 has a "lower" end 80 and an "upper" end 82. In the context of the present application, the terms "lower" and "upper" are used interchangeably with the terms "inflow" and "outflow", respectively. Thus, for example, the lower end 80 of the valve is its inflow end and the upper end 82 of the valve is its outflow end.

Prosthetic valve 10 and frame 12 are configured to be radially collapsible to a collapsed or crimped state for introduction into the body on a delivery catheter and radially expandable to an expanded state for implanting the valve at a desired location in the body (e.g., the native aortic valve). Frame 12 can be made of a plastically-expandable material that permits crimping of the valve to a smaller profile for delivery and expansion of the valve using an expansion device such as the balloon of a balloon catheter. Exemplary plastically-expandable materials that can be used to form the frame are described below. Alternatively, prosthetic valve 10 can be a so-called self-expanding valve wherein the frame is made of a self-expanding material such as Nitinol. A self-expanding valve can be crimped to a smaller profile and held in the crimped state with a restraining device such as a sheath covering the valve. When the valve is positioned at or near the target site, the restraining device is removed to allow the valve to self-expand to its expanded, functional size.

Figure 5:
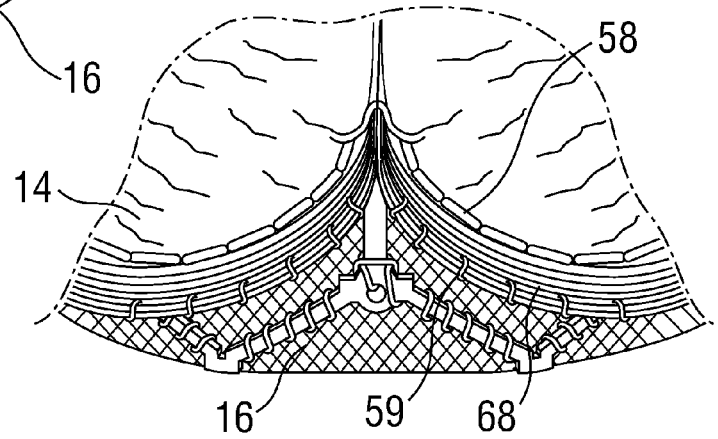
FIG. 5 is a bottom perspective view of the prosthetic valve of FIG. 1 showing the inside of the valve.
Figure 7:
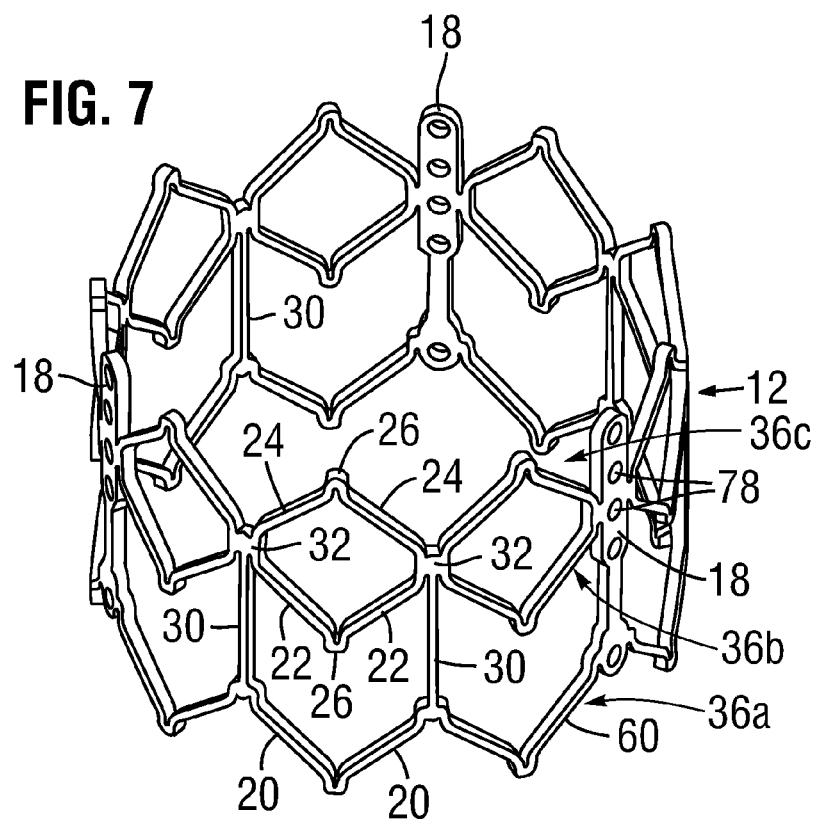
FIG. 7 is a perspective view of the frame of the prosthetic valve of FIG. 1.

Referring also to FIG. 7 (which shows the frame alone for purposes of illustration), frame 12 is an annular, stent-like structure having a plurality of angularly spaced, vertically extending, commissure attachment posts, or struts, 18. Posts 18 can be interconnected via a lower row 36a of circumferentially extending struts 20 and first and second rows upper rows 36b, 36c, respectively, of circumferentially extending struts 22 and 24, respectively. The struts in each row desirably are arranged in a zig-zag or generally saw-tooth like pattern extending in the direction of the circumference of the frame as shown. Adjacent struts in the same row can be interconnected to one another as shown in FIGS. 1 and 5 to form an angle A, which desirably is between about 90 and 110 degrees, with about 100 degrees being a specific example. The selection of angle A between approximately 90 and 110 degrees optimizes the radial strength of frame 12 when expanded yet still permits the frame 12 to be evenly crimped and then expanded in the manner described below.

In the illustrated embodiment, pairs of adjacent circumferential struts in the same row are connected to each other by a respective, generally U-shaped crown structure, or crown portion, 26. Crown structures 26 each include a horizontal portion extending between and connecting the adjacent ends of the struts such that a gap 28 is defined between the adjacent ends and the crown structure connects the adjacent ends at a location offset from the strut's natural point of intersection. Crown structures 26 significantly reduce residual strains on the frame 12 at the location of struts 20, 22, 24 during crimping and expanding of the frame 20 in the manner described below. Each pair of struts 22 connected at a common crown structure 26 forms a cell with an adjacent pair of struts 24 in the row above. Each cell can be connected to an adjacent cell at a node 32. Each node 32 can be interconnected with the lower row of struts by a respective vertical (axial) strut 30 that is connected to and extends between a respective node 32 and a location on the lower row of struts 20 where two struts are connected at their ends opposite crown structures 26.

In certain embodiments, lower struts 20 have a greater thickness or diameter than upper struts 22, 24. In one implementation, for example, lower struts 20 have a thickness $T_L$ (FIG. 9) of about 0.42 mm and upper struts 22, 24 have a thickness $T_U$ of about 0.38 mm. Because there is only one row of lower struts 20 and two rows of upper struts 22, 24 in the illustrated configuration, enlargement of lower struts 20 with respect to upper struts 22, 24 enhances the radial strength of the frame at the lower area of the frame and allows for more uniform expansion of the frame.

FIG. 9 shows a flattened view of a 120-degree segment of frame 12 shown in FIG. 7, the segment comprising a portion of the frame extending between two posts 18. As shown, the frame segment has three columns 34 and three rows 36a, 36b, 36c of struts per segment. Each column 34 is defined by the adjoining pairs of struts 20, 22, 24 extending between two axially extending struts 18, 30. Frame 12 desirably is comprised of three 120-degree segments, with each segment being bounded by two posts 18. Accordingly, frame 12 in the illustrated embodiment includes 9 total columns per frame.

The number of columns and rows desirably is minimized to reduce the overall crimp profile of the valve, as further discussed below. The arrangement of FIGS. 7 and 9 typically is used for valves that are less than about 29 mm in diameter, and are most suitable for valves that are about 20-26 mm in diameter. In working examples of valves comprising frame 12, a 20-mm valve can be crimped to a diameter of about 17 Fr, a 23-mm valve can be crimped to a diameter of about 18 Fr and a 26-mm valve can be crimped to a diameter of about 19 Fr. For valves that are about 29 mm and larger in diameter, it may be desirable to add another row and column of struts.

Figure 8:
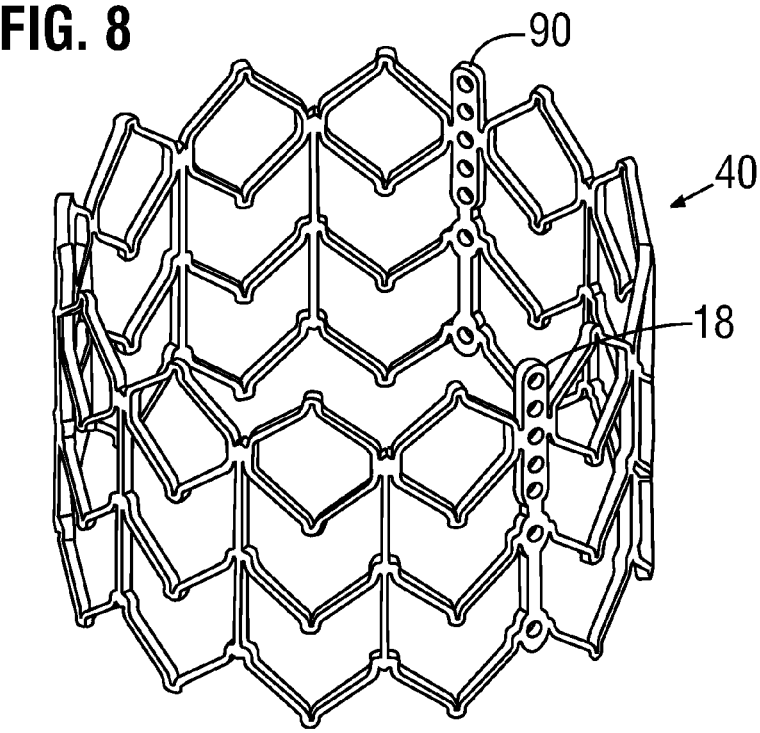
FIG. 8 is a perspective view of an alternative embodiment of a frame that can be used in the prosthetic valve of FIG. 1.

For example, FIGS. 8 and 10 show an alternative frame 40 that is similar to frame 12 except that frame 40 has four rows of struts (a lowermost, first row 52a of struts 42, a second row 52b of struts 44, a third row 52c of struts 46, and an uppermost row 52d of struts 48) instead of three rows of struts, as well as four columns 50 of struts for each 120-degree frame segment instead of three columns of struts. FIG. 10 shows a flattened view of a 120-degree segment of frame 40 shown in FIG. 8. Frame 40 in the illustrated embodiment includes three such 120-degree segments, providing 12 total columns 50 of struts for the frame.

Struts 46 of the third row desirably are facing in the opposite direction of the struts 48 of the fourth row (i.e., the apexes or crown portions are facing in the opposite direction), to help avoid buckling of the vertical posts of the frame during crimping and expansion of the valve. Struts 44 of the second row can be arranged so as to be facing in the same direction as the struts 42 of the first row as shown (i.e., the apexes or crown portions are facing in the same direction). Alternatively, struts 44 of the second row can be facing in the opposing direction from struts 42 of the first row so as to form square cells, like the cells formed by the struts 46, 48 of the third and fourth rows, respectively. Frame 40 can also include axially extending struts 54 connected to and extending between the ends of each strut 42, 44, 46, and 48 aligned in a column 50 that are not connected to a post 18. As noted above, frame 40 is most suitable for valves 29 mm and larger in diameter (when expanded to its functional size). In a working example of a valve incorporating frame 40, a 29-mm valve can be crimped to a diameter of about 21 Fr.

Suitable plastically-expandable materials that can be used to form the frame include, without limitation, stainless steel, a nickel based alloy (e.g., a nickel-cobalt-chromium alloy), polymers, artificially stiffened textiles or combinations thereof. In the case of a frame formed with an artificially stiffened textile, in one preferred embodiment, a fabric may be treated with a boron nano-tube ink solution. The resulting component preferably embodies the characteristics of both the original fabric material and boron carbide, which is a stiff, yet bendable and flexible material. In an alternative textile configuration, a fabric may be impregnated with metal. In yet another configuration, composite carbon fibers may be formed into sheets that could be fabricated into a generally cylindrical body. Finally, a frame may be formed by weaving metal or other stiffening fibers into a textile during fabrication.

However, in preferred embodiments, frame 20 is made of a nickel-cobalt-chromium-molybdenum alloy, such as MP35N™ (trade name of SPS Technologies), which is equivalent to UNS R30035 (covered by ASTM F562-02). MP35N™/UNS R30035 comprises 35% nickel, 35% cobalt, 20% chromium, and 10% molybdenum, by weight. It has been found that the use of MP35N to form frame 20 provides superior structural results over stainless steel. In particular, when MP35N is used as the frame material, less material is needed to achieve the same or better performance in radial and crush force resistance, fatigue resistances, and corrosion resistance. Moreover, since less material is required, the crimped profile of the frame can be reduced, thereby providing a lower profile valve assembly for percutaneous delivery to the treatment location in the body.

Referring again to FIG. 1, skirt 16 can be formed, for example, of polyethylene terephthalate (PET) ribbon. The thickness of the skirt can vary, but is desirably less than 6 mil, and desirably less than 4 mil, and even more desirably about 2 mil. Skirt 16 can be secured to the inside of frame 12 via polytetrafluoroethylene (PTFE) sutures 56, as shown in FIG. 1. The skirt comprises a single sheet of material that extends continuously around the leaflet structure. Leaflet structure 14 can be attached to the skirt via a thin PET reinforcing strip 68 (or sleeve), discussed below, which enables a secure suturing and protects the pericardial tissue of the leaflet structure from tears. Leaflet structure 14 can be sandwiched between skirt 16 and the thin PET strip 68 as shown. Suture 58, which secures the PET strip and the leaflet structure 14 to skirt 16, can be any suitable suture, such as an Ethibond suture. Suture 58 desirably tracks the curvature of the bottom edge of leaflet structure 14, as described in more detail below. Leaflet structure 14 can be formed of bovine pericardial tissue, biocompatible synthetic materials, or various other suitable natural or synthetic materials as known in the art and described in U.S. Pat. No. 6,730,118, which is incorporated by reference herein.

Figure 6:
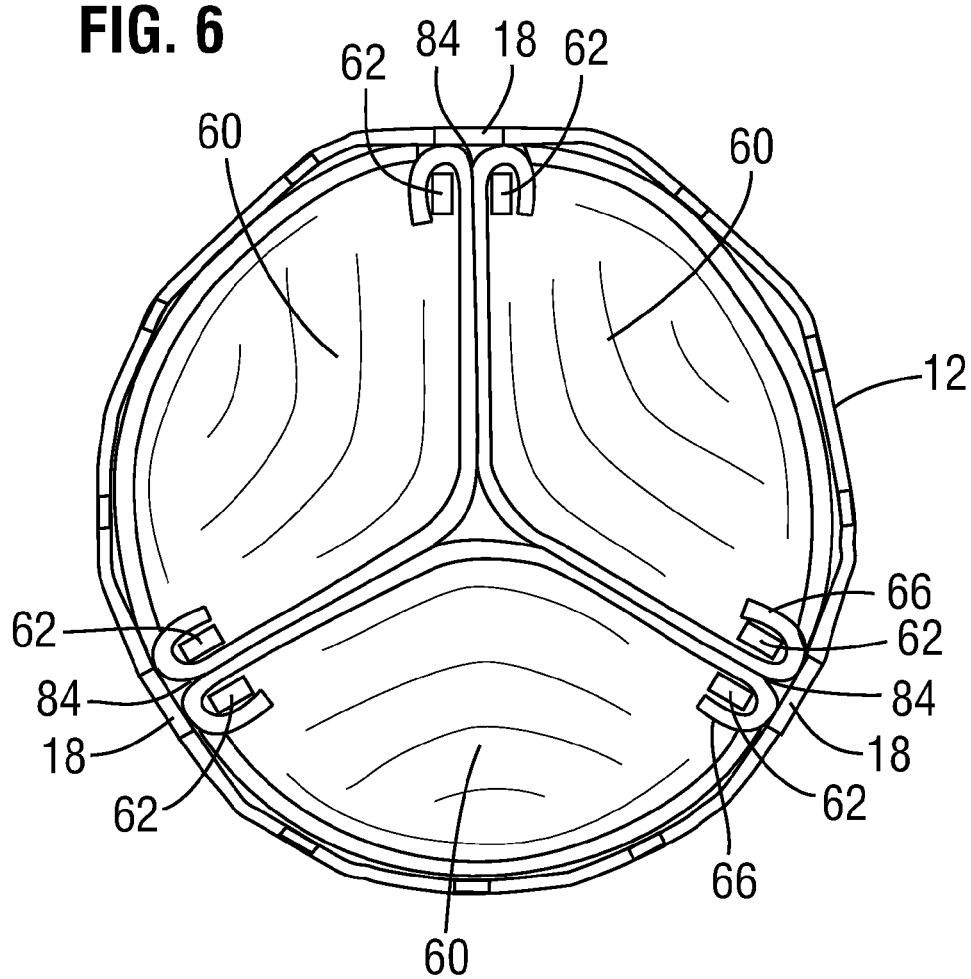
FIG. 6 is a top plan view of the prosthetic valve of FIG. 1.

Leaflet structure 14 can comprise three leaflets 60, which can be arranged to collapse in a tricuspid arrangement, as best shown in FIGS. 2 and 6. The lower edge of leaflet structure 14 desirably has an undulating, curved scalloped shape (suture line 58 shown in FIG. 1 tracks the scalloped shape of the leaflet structure). By forming the leaflets with this scalloped geometry, stresses on the leaflets are reduced, which in turn improves durability of the valve. Moreover, by virtue of the scalloped shape, folds and ripples at the belly of each leaflet (the central region of each leaflet), which can cause early calcification in those areas, can be eliminated or at least minimized. The scalloped geometry also reduces the amount of tissue material used to form leaflet structure, thereby allowing a smaller, more even crimped profile at the inflow end of the valve.

Leaflets 60 can be secured to one another at their adjacent sides to form commissures 84 of the leaflet structure (the edges where the leaflets come together). Leaflet structure 14 can be secured to frame 12 using suitable techniques and mechanisms. For example, as best shown in FIG. 6, commissures 84 of the leaflet structure desirably are aligned with the support posts 18 and secured thereto using sutures. The point of attachment of the leaflets to the posts 18 can be reinforced with bars 62 (FIG. 11), which desirably are made of a relatively rigid material (compared to the leaflets), such as stainless steel.

Figure 12:
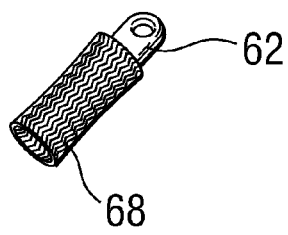
FIG. 12 is a perspective view of the reinforcing bar of FIG. 11 and a PET sleeve that can be used to cover the bar.
Figure 13:
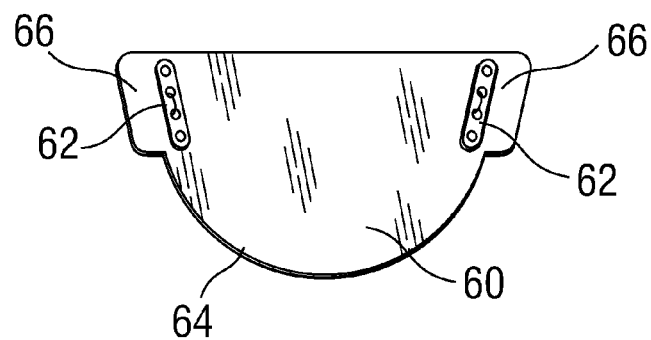
FIG. 13 is a flattened view of a leaflet of the valve shown in FIG. 1.
Figure 18:
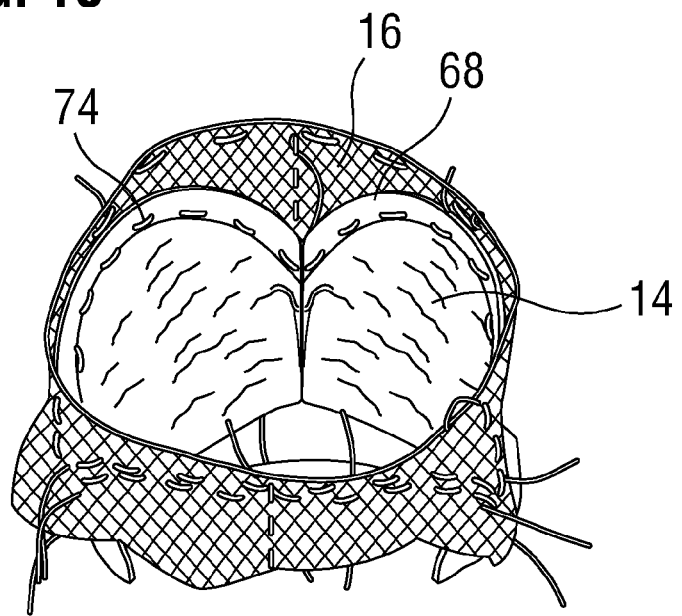
FIG. 18 is a bottom perspective view of the leaflet structure connected to the skirt so as to form a leaflet assembly.

FIG. 13 shows a single leaflet 60, which has a curved lower edge 64 and two tabs 66 extending between the upper edge and curved lower edge of the leaflet. The curved lower edge 64 forms a single scallop. When secured to two other leaflets to form leaflet structure 14, the curved lower edges of the leaflets collectively form the scalloped shaped lower edge portion of the leaflet structure (as best shown in FIG. 18). As further shown in FIG. 13, two reinforcing bars 62 can be secured to the leaflet adjacent to tabs 66 (e.g., using sutures). The tabs can then be folded over bars 62 and secured in the folded position using sutures. If desired, as shown in FIG. 12, each bar 62 can be placed in a protective sleeve 86 (e.g., a PET sleeve) before being secured to a leaflet.

Figure 14:
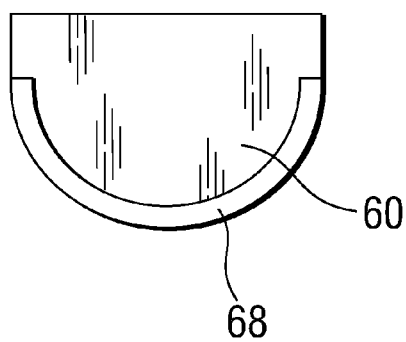
FIG. 14 is a flattened view of the opposite side of the leaflet showing a reinforcing strip secured adjacent the bottom edge of the leaflet.
Figure 15:
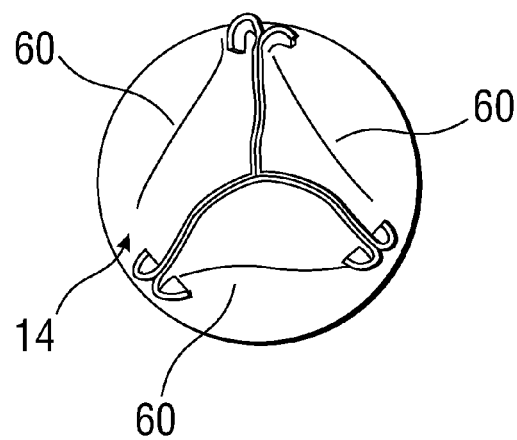
FIG. 15 is a top plan view of the leaflet structure of the valve of FIG. 1 prior to attachment to the frame.

As shown in FIG. 14, the lower curved edge 64 of the leaflet can be reinforced for later securement to the skirt 16, such as by securing a reinforcing strip 68 along the curved lower edge between tabs 66 on the side of the leaflet opposite bars 62. Three such leaflets 60 can be prepared in the same manner and then connected to each other at their tabs 66 in a tricuspid arrangement to form leaflet structure 14, as shown in FIG. 15. The reinforcing strips 68 on the leaflets collectively define a ribbon or sleeve that extends along the lower edge portion of the inside surface of the leaflet structure.

As noted above, leaflet structure 14 can be secured to frame 12 with skirt 16. Skirt 16 desirably comprises a tough, tear resistant material such as PET, although various other synthetic or natural materials can be used. Skirt 16 can be much thinner than traditional skirts. In one embodiment, for example, skirt 16 is a PET skirt having a thickness of about 0.07 mm at its edges and about 0.06 mm at its center. The thinner skirt can provide for better crimping performances while still providing good perivalvular sealing.

Figure 16:
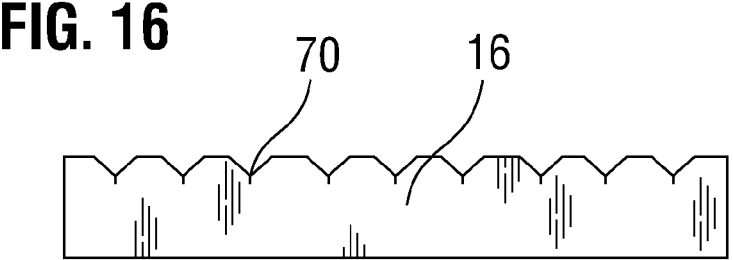
FIG. 16 is a flattened view of the skirt used in the valve shown in FIG. 1.
Figure 17:
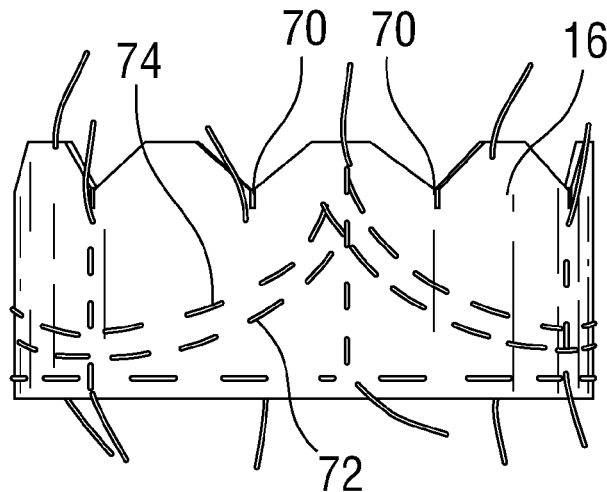
FIG. 17 is a side elevation view of the skirt of FIG. 16 after being sewn into an annular shape.

FIG. 16 shows a flattened view of the skirt before the opposite ends are secured to each other to form the annular shape shown in FIG. 17. As shown, the upper edge of skirt 16 desirably has an undulated shape that generally follows the shape of the second row of struts 22 of the frame. In this manner, the upper edge of skirt 16 can be tightly secured to struts 22 with sutures 56 (as best shown in FIG. 1). Skirt 16 can also be formed with slits 70 to facilitate attachment of the skirt to the frame. Slits 70 are aligned with crown structures 26 of struts 22 when the skirt is secured to the frame. Slits 70 are dimensioned so as to allow an upper edge portion of skirt to be partially wrapped around struts 22 and reduce stresses in the skirt during the attachment procedure. For example, in the illustrated embodiment, skirt 16 is placed on the inside of frame 12 and an upper edge portion of the skirt is wrapped around the upper surfaces of struts 22 and secured in place with sutures 56. Wrapping the upper edge portion of the skirt around struts 22 in this manner provides for a stronger and more durable attachment of the skirt to the frame. Although not shown, the lower edge of the skirt can be shaped to conform generally to the contour of the lowermost row of struts 22 to improve the flow of blood past the inflow end of the valve.

As further shown in FIG. 17, various suture lines can be added to the skirt to facilitate attachment of the skirt to the leaflet structure and to the frame. For example, a scalloped shaped suture line 72 can be used as a guide to suture the lower edge of the leaflet structure at the proper location against the inner surface of the skirt using suture 59 (as best shown in FIG. 5). Another scalloped shaped suture line 74 (FIG. 17) can be used as a guide to suture the leaflet structure to the skirt using sutures 58 (FIG. 1). Reinforcing strips 68 secured to the lower edge of the leaflets reinforces the leaflets along suture line 58 and protects against tearing of the leaflets. FIG. 18 shows a leaflet assembly comprised of skirt 16 and leaflet structure 14 secured to the skirt. The leaflet assembly can then be secured to frame 12 in the manner described below. In alternative embodiments, the skirt, without the leaflet structure, can be connected to the frame first, and then the leaflet structure can be connected to the skirt.

FIG. 6 shows a top view of the valve assembly attached to frame 12. Leaflets 60 are shown in a generally closed position. As shown, the commissures of the leaflets are aligned with posts 18 of the frame. The leaflets can be secured to the frame using sutures extending through tabs 66 of the leaflets, openings 76 in bars 62, and openings 78 in posts 18, effectively securing tabs 66 to posts 18. As noted above, bars 62 reinforce the tabs at the area of connection with posts and protect against tearing of the leaflets.

Figure 6A:
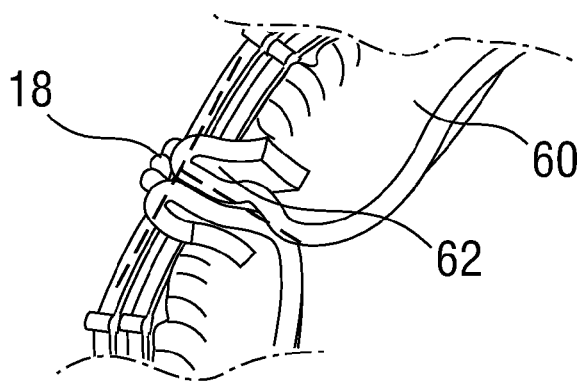
FIG. 6A is an enlarged partial top view of the valve of FIG. 1 illustrating the positioning of the reinforcing bars with respect to the commissure attachment posts of the frame.

As shown in FIG. 6A, bars 62 desirably are aligned perpendicular and as straight as possible with respect to posts 18 of the frame, such that bars 62 and post 18 at each commissure form a "T" shape. The width of bars 62 and the attachment of the commissures via the bars provides a clearance between the deflectable portions of the leaflets 60 (the portions not secured by sutures to the frame) and the frame, while the edge radius (thickness) of bars 62 serves as a flex hinge for the leaflets 60 during valve opening and closing, thereby increasing the space between the leaflets and the frame. By increasing the space between the moving portions of the leaflets and frame and by having the leaflets flex against an edge radius of bars 62, contact between the moving portions of the leaflets (especially the outflow edges of the leaflets) and the frame can be avoided during working cycles, which in turn improves the durability of the valve assembly. This configuration also enhances perfusion of blood through the coronary arteries.

Some disclosed prosthetic valve embodiments are constructed without rigid bars at the commissures. Removing the bars 62 can allow a valve to be crimped to a smaller diameter. However, it is desirable to replace the functions of the bars 62 when they are removed. These functionalities can include reinforcement of the commissure sutures, guiding of the commissure sutures, and creating a clearance space between the frame and the moving parts of the leaflets. To replace these functions of the bars 62, for example, the leaflet tabs can be folded and/or rolled in various commissure configurations. In addition, non-rigid reinforcing materials can also be added to the commissures to replace the functions of the bars 62.

Figure 19:
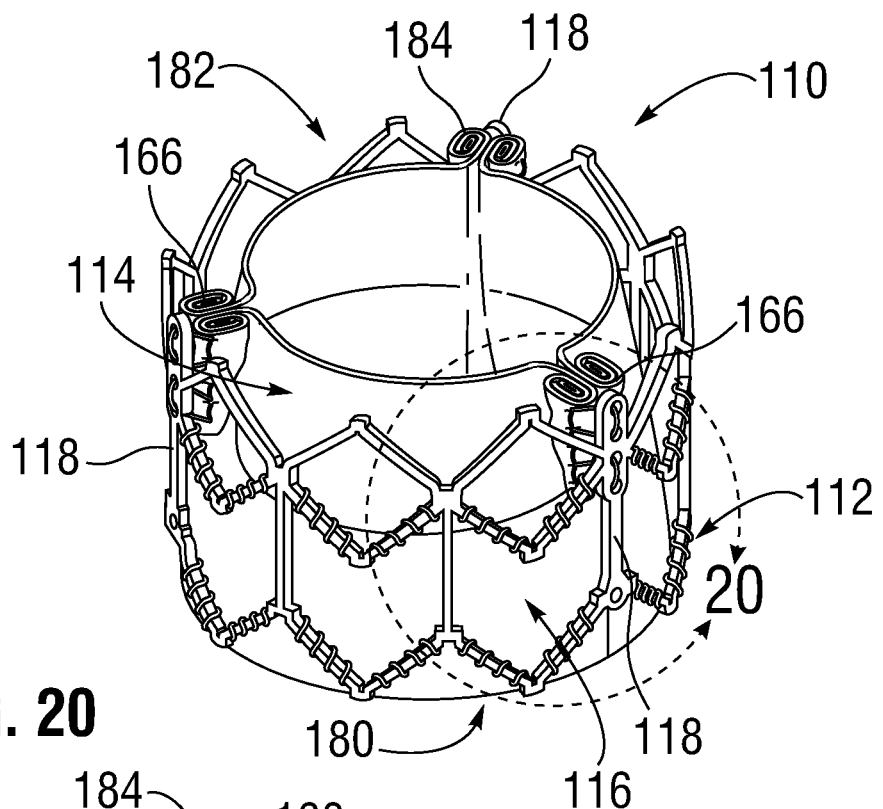
FIG. 19 is a perspective view of an embodiment of a prosthetic heart valve having commissures comprising leaflet side tabs rolled into spirals.
Figure 20:
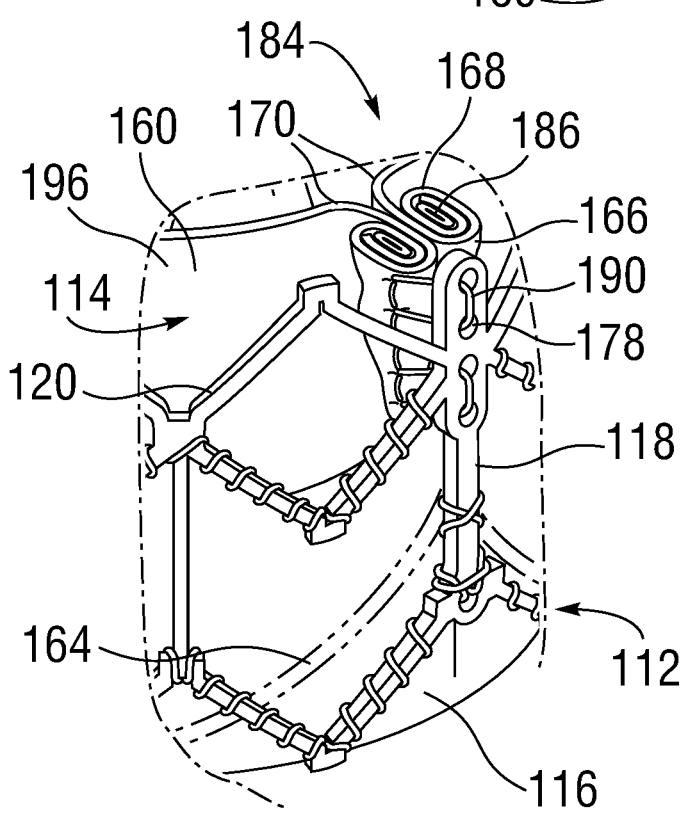
FIG. 20 is an enlarged, perspective view of a commissure of the valve of FIG. 19.

FIGS. 19 and 20 show an embodiment of an implantable prosthetic valve 110 having spiraled side tabs 166 at commissures 184. The valve 110 can comprise a frame 112, a leaflet structure 114 supported by the frame, and a skirt 116 secured between the frame and the leaflet structure. Valve 110 has a lower, inflow end 180 and an upper, outflow end 182.

The frame 112 can be annular and can comprise a plurality of longitudinally aligned, angularly spaced commissure attachment posts 118 interconnected by struts 120. Each post 118 can comprise one or more openings 178 that can be used to secure the commissures 184 to the frame 112. The valve 110 and frame 112 can be radially collapsible and expandable as described above with reference to the prosthetic valve 10 and frame 12. The frame 112 can be the same as or substantially similar to the frame 12. In other embodiments, the frame can be without attachment posts 118 and openings 178. In these embodiments, the commissures 184 can be secured to the skirt 116 rather than to the frame, as shown in FIG. 23 for example.

The leaflet structure 114 can comprise a plurality of leaflets 160 each comprising two opposing side tabs 166, a curved lower edge 164 extending between the side tabs, and an upper articulation portion 196. Each side tab 166 is rolled into a spiral 168 and each spiral is secured to an adjacent spiral of an adjacent leaflet 160 to form a respective commissure 184. Each commissure 184 can be secured to a respective commissure attachment post 118 of the frame. The spirals 168 can be secured to one another and to the posts 118 with sutures and/or other suitable attachment mechanisms. Preferably the side tab of each spiral is rolled around a central longitudinal axis of the spiral greater than 360 degrees such that at least two layers of the side tab are in contact with each other.

Each spiral 168 can comprise a non-rigid reinforcing material that can reinforce the spirals to resist suture tear-through when the spirals are sutured to one another and/or sutured to the frame 112. The reinforcing material can comprise a plurality of flexible inserts 186, as shown in FIGS. 19-24. In some embodiments, one insert 186 is positioned within each spiral 168, such as at the center of each spiral, as best shown in FIG. 22. In some embodiments, the inserts 186 comprise a tube or sleeve of reinforcing material, as shown in FIG. 23. The inserts 186 can comprise flexible yet tear-resistant material, such as woven fabric. The inserts 186 can comprise a variety of natural and/or synthetic biocompatible materials. Exemplary synthetic materials can include polymers such as nylon, silicone, and polyesters, including PET. Exemplary natural materials can include animal tissue, such as bovine, porcine, and equine tissue, including pericardial tissue. Various other synthetic or natural materials can be also used. The reinforcing material of the inserts 186 can have a thickness between about 0.006 inches and about 0.020 inches. The axial length of the inserts 186 can similar to the axial length of the side tabs 166. The width of the insert can be in a range between about 0.016 inches and about 0.047 inches.

As shown in FIG. 24, during assembly of the leaflet structure, one or more inserts 186 can be temporarily secured to each side tab 166 of each leaflet 160, each leaflet comprising a separate piece of material, such as with sutures 192. The side tabs 166 can then be rolled up around the inserts 186 to form spirals 168 on each side of the leaflet 160. A template, or jig, 194, such as the embodiment shown in FIG. 25, can be used to guide the temporary suturing of the inserts to the side tabs and the rolling of the spirals 168. The dashed line labeled 160 in FIG. 25 shows the position of a leaflet 160 on the template 194 such that the perimeter of the leaflet is aligned with openings 138 in the template. The dashed lines 186 show where the inserts 186 can be sutured to the leaflets with permanent or temporary sutures using the guide holes 140 in the template. The side tabs 166 of the leaflet can then be rolled or folded around the inserts 186 such that the insert is aligned with the openings 144 of the template. The spirals can then be sutured in place with permanent or temporary sutures using the guide holes 142. The temporary sutures can be removed after a pair of spirals are secured together with a suture 188 to form the commissure 184.

The number of loops the side tabs 166 form around the inserts 186 can affect the size and strength of the spirals 168. Desirably, the side tabs 166 form at least one complete loop around the inserts 186. The spirals 168 can be rolled differently to increase the number of side tab layers that encircle the inserts 186, which can increase the size of the spiral. In the embodiment shown in FIG. 22, the spirals 168 form slightly more than one and a half full loops around the inserts 186 and are sutured together at the dashed suture line 188. The sutures 188 can be oriented generally perpendicular to the radius of the frame and can pass circumferentially back and forth through the spirals 168 at a plurality of different longitudinal positions, as shown in FIG. 21. The sutures 188 can intersect multiple layers of each side tab 166 and the inserts 186 with each pass, thereby utilizing the inserts to reinforce the sutures. As shown in FIG. 22, each stitch of suture 188 can intersect four layers of each side tab 166 and two layers of each insert 186. More specifically, each stitch of suture 188 can intersect a first two layers of a first spiral 168, two layers of tubular insert 186 within the first spiral, a second two layers of the first spiral, a first two layers of a second spiral 168, two layers of a tubular insert 186 within the second spiral, and a second two layers of the second spiral, in that order.

The sutures 188 are sewn tightly to secure the spirals 168 together and avoid leakage through the commissures 184. The sutures 188 can cause the spirals 168 to collapse and/or compress together in the direction of the sutures. FIG. 22 shows the spirals in a loose configuration before suturing and FIGS. 20 and 21 show the spirals in a collapsed and/or compressed configuration after suturing.

The commissures 184 can be sutured to the posts 118 to secure the leaflet structure 114 within the frame 112. As shown in FIG. 20, sutures 190 can pass through the commissures 184 and through the openings 178 in the posts 118 to secure the commissures to the posts.

FIG. 23 shows an alternative suturing pattern having the spirals 168 sutured to the skirt 116. In this embodiment, the skirt 116 can extend between the frame 112 and the commissures 184. Sutures 189 can secure the spirals 168 to the skirt 116 and thereby suspend the leaflet structure 114 within the skirt. The skirt 116 can be secured to the frame 112 independently of the commissures 184, such as by a separate set of sutures. This construction can be used with a frame 112 that does not have distinct commissure attachment posts 118 because the skirt 116 can be attached to the frame around the entire perimeter of the skirt.

Each stitch of sutures 189 can be oriented generally perpendicular to the frame and can pass radially in and out through the centers of the spirals 168 at a plurality of different longitudinal positions. The sutures 189 can intersect multiple layers of the side tab 166, the insert 186, and the skirt 116 with each pass, thereby utilizing the insert and the skirt to reinforce the sutures. As shown in FIG. 23, each stitch of suture 189 can intersect four layers of each side tab 166, two layers of each insert 186, and a skirt layer 116. More specifically, each stitch of each suture 189 can intersect a first two layers of a spiral 168, two layers of a tubular insert 186 within the spiral, a second two layers of the spiral, and a skirt layer, in that order moving radially outward.

The radially oriented sutures 189 can replace or supplement the circumferentially oriented sutures 188. In embodiments where the sutures 188 are not included, the two spirals of each commissure can still be secured tightly together by locating the sutures 189 sufficiently close together such that the adjacent leaflet tabs are compressed together. Furthermore, the skirt 116 can act as an additional leak prevention mechanism should any fluid leak through the commissures 184.

In operation, articulation portions 196 of the leaflets 160 move radially outwardly and inwardly to open and close, respectively, the valve structure 114 and regulate the flow of blood through the valve 110. As the articulation portions 196 flex in and out, the spiraled side tabs 166 can stay relatively motionless. The articulation portions 196 bend about respective flex hinges 170 on each side of the leaflets 160 adjacent to the side tabs 166, as shown in FIG. 21. As the articulation portions move, the flex hinges 170 can bear against curved surfaces 172 of the respective spirals 168. Each curved surface 172 can be a portion of a leaflet side tab 166 and thus provide a rounded, cushioned, non-abrasive surface for the respective flex hinge 170 to bear against. This can reduce damage to the leaflets 160 at the flex hinges 170 and prolong the life of the valve 110.

The radial diameter of the spirals 168 can provide a radial clearance between the frame 112 and the articulation portions 196 of the leaflets. This clearance can reduce the amount of contact between the leaflets 160 and the frame 112, thereby reducing damage to the leaflets caused by contact with the frame.

The spirals 168, being compressed by sutures 188 and/or 189, can furthermore keep the sutures 188 spaced away from the articulation portions 196 of the leaflets 160. When the spirals are compressed together by sutures 188, as shown in FIG. 21, only the portions of the leaflets 160 radially inward of the hinge line 174 shown in FIG. 22 are free to articulate while the portions of the leaflets radially outward from the hinge line 174 remain relatively stationary. The distance between the hinge line 174 and the suture line 188 represents the spacing between the sutures 188 and the articulation portions 196 of the leaflets. When the leaflets 160 are forced open by a surge of blood flowing through the valve 110, the blood pressure can cause the leaflets to pull apart from one another other, causing a stress on the commissures 184 that urges the two spirals 168 apart from one another. This stress is concentrated at the hinge line 174. Because the hinge line 174 is spaced from the suture line 188, much of the stress is transferred from the flex hinges 170 to the curved surfaces 172 of the spirals 168 and spread across the various layers of the spirals before being transferred to the sutures. This can allow the compressible spiral material to absorb much of the stress before it reaches the suture line and thereby reduce the likelihood of the sutures 188 tearing through the side tab material.

In some embodiments, the leaflets 160 can comprise bovine pericardium. Tissue can be harvested from bovines aged less than about four weeks. In some embodiments, the tissue is harvested from bovines aged between about one week and about two weeks. These animals offer a thinner, yet durable pericardium material that can allow the spirals 168 to be rolled with more layers for a desired spiral diameter, which can improve strength and durability. The thin yet durable material can furthermore allow for the valve 110 to be collapsible to a smaller overall diameter. The harvested material can be fixed in glutaraldehyde or other fixation solution suitable for bioprosthetic tissue applications.

Figure 26:
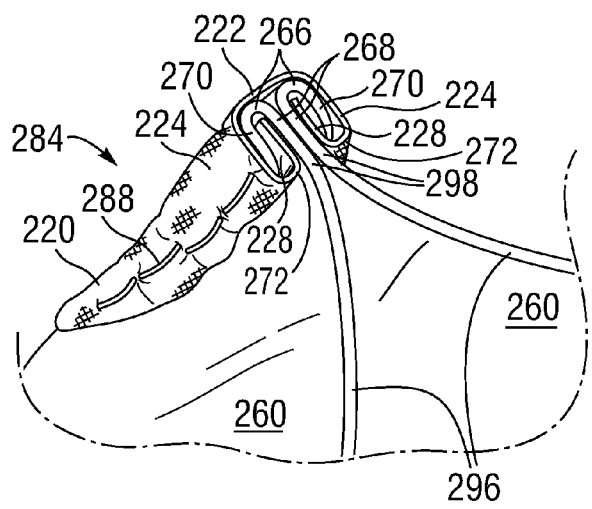
FIG. 26 shows an alternative commissure embodiment having a reinforcing sheet folded around the side tabs.
Figure 27:
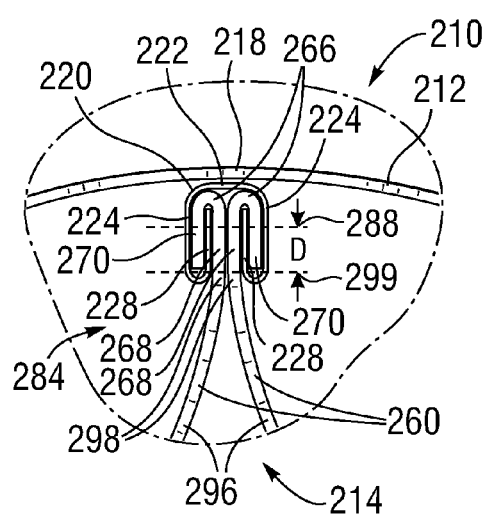
FIG. 27 is a top view of the commissure of FIG. 26 showing an exemplary radial spacing between a suture line and a flex hinge line.
Figure 29:
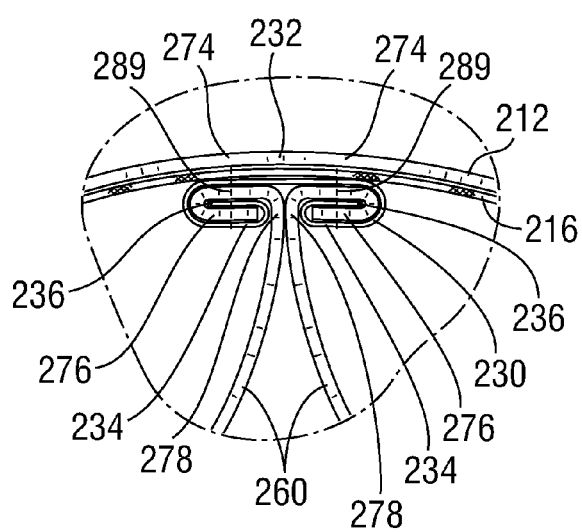
FIG. 29 is a top view of a commissure of an alternative valve embodiment, wherein folded side tabs are sutured to an annular skirt via a reinforcing sheet.

FIGS. 26 and 27 show an embodiment of an implantable prosthetic valve 210 comprising cloth-covered commissures 284. The valve 210 comprises a frame 212 and a leaflet structure 214 supported within the frame. The commissures 284 are sutured to posts 218 to secure the leaflet structure 214 to the frame 212. The valve 210 and frame 212 can be radially collapsible and expandable as described with reference to the prosthetic valve 10 and frame 12. The frame 212 can be the same as or substantially similar to frames 12 and 112. In other embodiments, the frame 212 can be without attachment posts 218. In these embodiments, the commissures 284 can be secured to a skirt 216, as shown in FIG. 29 for example.

The leaflet structure 214 can comprise a plurality of leaflets 260 and a plurality of reinforcing sheets 220. Each leaflet 260 comprises two opposing side tabs 266 and an articulation portion 296 between the side tabs. Each side tab 266 is secured to an adjacent side tab of another leaflet and to one or more of the reinforcing sheets 220 to form the commissures 284. Each commissure 284 is secured to a respective commissure attachment post 218 of the frame 212. The side tabs 266 can be secured to one another and to the posts 118 with sutures and/or other suitable attachment mechanisms.

As shown in FIG. 27, each side tab 266 comprises a medial portion 268 and an end portion 270 extending from the medial portion. The medial portions 268 of adjacent side tabs 266 can be in contact with one another at the center of the commissures 284. The end portions 270 can be folded back away from each other and adjacent to the medial portions 268, creating an approximately 180° fold between the medial and end portions.

In some embodiments, a single reinforcing sheet 220 reinforces each commissure 284, as shown in FIG. 26. The sheets 220 can comprise a flexible, tear resistant material, including a variety of natural and/or synthetic biocompatible materials. Exemplary synthetic materials can include polymers such as nylon, silicone, and polyesters, including PET. In one example, the sheets 220 comprise a woven PET fabric.

Figure 28:
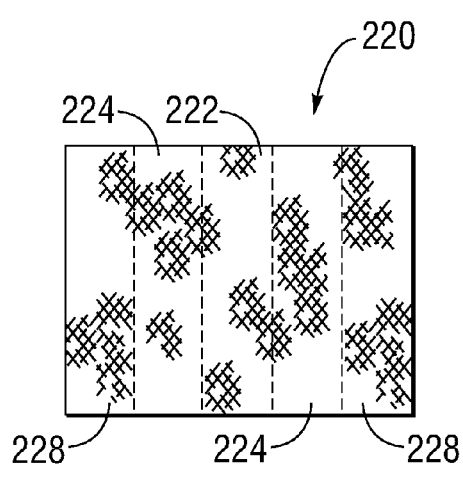
FIG. 28 shows the reinforcing sheet of FIG. 26 laid flat.

As shown in FIG. 28, each reinforcing sheet 220 can be generally rectangular (when laid flat) and can comprise a middle portion 222, side portions 224, and end portions 228. As best shown in FIG. 27, the middle portion 222 of each sheet 220 can extend circumferentially between the side tabs 266 and the commissure post 218 of the frame 212. The side portions 224 can extend radially inwardly from opposing sides of the middle portion 222 and around the end portions 270 of the side tabs. The end portions 228 of the sheet can extend radially outwardly from the inner ends of the side portions 224 of the sheet. Each end portion 228 of the sheet is sandwiched between the medial portion 268 and the end portion 270 of a respective side tab. Similarly, the end portions 270 of the side tabs are sandwiched between the side portions 224 of the sheet and the end portions 228 of the sheet.

Each commissure 284 can be secured together by one or more sutures 288. The sutures 288 can be oriented generally perpendicular to the radius of the frame and can pass circumferentially back and forth through the commissure 284 at a plurality of different longitudinal positions, as shown in FIG. 26. The suture line 288 shown in FIG. 27 represents the radial position of the sutures 288 relative to the frame. Each suture 288 can intersect the medial portions 268 and the end portions 270 of both side tabs 266, and intersect both side portions 224 and both end portions 228 of the reinforcing sheet 220. More specifically, as shown in FIG. 27, each suture 288 can intersect a first sheet side portion 224, a first side tab end portion 270, a first sheet end portion 228, a first side tab medial portion 268, a second side tab medial portion 268, a second sheet end portion 228, a second side tab end portion 270, and a second sheet side portion 224, in that order.

FIG. 29 shows an alternative sheet-covered commissure embodiment. Sutures 289 can secure the commissure 284 to the skirt 216 and thereby suspend the leaflet structure within the skirt independent of the frame 212. This construction can be used with a frame that does not have distinct commissure attachment posts because the skirt can be attached to the frame around the entire perimeter of the skirt.

As shown in FIG. 29, each leaflet side tab 266 can comprise a medial portion 278, an outer portion 274, and an inner portion 276. The medial portions 278 of adjacent side tabs can extend radially side by side. The outer portions 274 can extend from the respective medial portions 260 circumferentially apart from one another. The inner portions 276 can extend from the respective outer portions 274 circumferentially toward one another and adjacent to the inner surface of the respective outer portion 274.

Each commissure can comprise a reinforcing sheet 230 comprising a middle portion 232, inner portions 234, and end portions 236. As shown in FIG. 29, the middle portion 232 of each sheet can extend circumferentially between the outer portions 274 of the side tabs and the skirt 216. The sheet 230 can extend from opposing sides of the middle portion 232 around the lateral surfaces of the folded side tabs and inner portions 234 of the sheet can extend circumferentially toward one another along the inner portions 276 of the side tabs. The sheet 230 can then extend from medial sides of the inner portions 234 around the ends of the side tabs and end portions 236 of the sheet can extend circumferentially away from one another between the inner portions 274 and outer portions 276 of the side tabs.

The sutures 289 can be oriented generally perpendicular to the circumference of the skirt 216 and can pass radially in and out through the commissures at a plurality of different longitudinal positions. Each stitch of the sutures 289 can intersect multiple layers of the side tab 266, the reinforcing sheet 230, and the skirt 216 with each pass, thereby utilizing the sheet and the skirt to reinforce the sutures. As shown in FIG. 29, each stitch of each suture 289 can intersect two layers of each side tab 266, three layers of the sheet 230, and a skirt layer 216. More specifically, each stitch of each suture 289 can intersect an inner portion 234 of the sheet, an inner portion 276 of a side tab, an end portion 236 of the sheet, an outer portion 274 of the side tab, the middle portion 232 of the sheet, and the skirt 216, in that order moving radially outward.

In embodiments using the radial sutures 289, the two halves of each commissure 284 can be secured tightly together by locating the sutures 289 sufficiently close together such that the adjacent medial portions 278 of the side tabs are compressed together. Furthermore, the middle portion 232 of the sheet and the skirt 216 can act as an additional leak prevention barriers should any fluid leak between the medial portions 278 of the side tabs.

During operation of the valve 210, the articulation portions 296 of the leaflets 260 flex between open and closed positions while the commissures 284 stay relatively motionless. Each articulation portion 296 flexes about flex hinges 298 adjacent to the side tabs 266 on either side of the leaflet 260. As the articulation portions 296 articulate, the flex hinges 298 can bear against curved surfaces 272 of the commissures 284. Each curved surface 272 is a portion of the reinforcing sheet 220 and provides a rounded, cushioned, non-abrasive surface for the respective flex hinge 298 to bear against. This can reduce damage to the leaflets 260 at the flex hinges 298 and prolong the life of the valve 210.

The radial diameter of the commissures 284 can provide a radial clearance between the frame 212 and the articulation portions 296 of the leaflets 260. This clearance can reduce the amount of contact between the leaflets 260 and the frame 212, thereby reducing damage to the leaflets caused by contact with the frame.

The commissures 284, being compressed by sutures 288, can furthermore keep the suture line 288 spaced away from the articulation portions 296 of the leaflets 260. As shown in FIG. 27, only the portions of the leaflets 260 radially inward of the hinge line 299 are free to articulate while the portions of the leaflets radially outward from the hinge line 299 remain relatively stationary. The distance D between the hinge line 299 and the suture line 288 represents the spacing between the sutures 288 and the articulation portions 296 of the leaflets.

Figure 30:
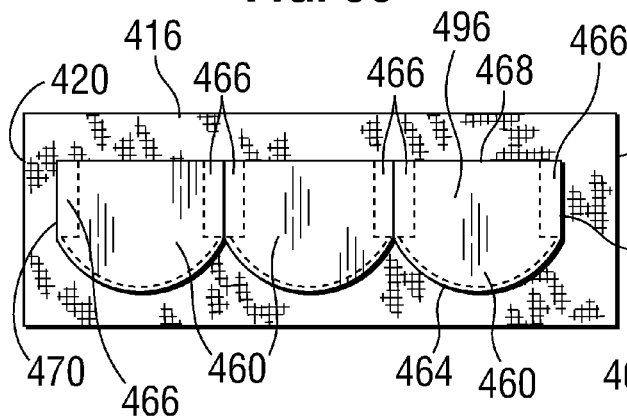
FIG. 30 shows three exemplary leaflets sutured to an exemplary flat sheet.

FIGS. 30-33 show an embodiment of a valve 410 having a modular construction. Leaflets 460 can be supported by a sleeve 418 to form an inner structure 414, which can then be sewn within a frame 412. In one exemplary method of assembling the valve 410, the leaflets 460 are first sewn to a flat sheet 416 of a tough, flexible material, such as woven PET fabric, as shown in FIG. 30. The leaflets 460 are sewn to the sheet 416 around the curved lower edges 464 while the upper edges 468 are left free to allow an articulation portion 496 to flex away from the sheet. Side tabs 466 of the leaflets 460 are folded between the articulation portion 496 and the sheet 418 and sewn to the sheet. The side tabs 466 can be sewn to the sheet 418 in various configurations, such as in spirals similar to side tabs 266.

Figure 31:
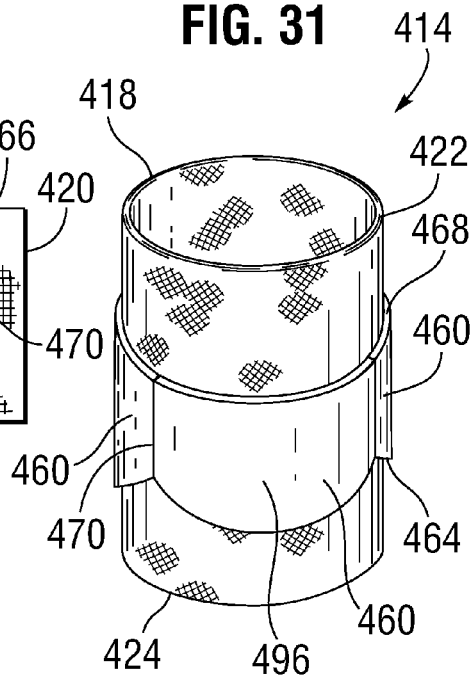
FIG. 31 is a perspective view of a sleeve formed by rolling the sheet of FIG. 30 into a cylinder.

Side portions 420 of the sheet 416 can then be sewn together to form a sleeve 418 having the leaflets 460 sewn around an outer circumference, as shown in FIG. 31. Free ends 470 of the leaflet assembly (see FIG. 30) can be positioned in contact with one another when the sheet 416 is formed into the sleeve 418, thereby creating a continuous ring of leaflets around the sleeve. The side portions 420 of the sheet can be trimmed and secured together to form the sleeve. The sleeve 418 and leaflets 460 can then be turned inside-out to form the inner structure 414 having the leaflets secured within the sleeve.

Figure 32:
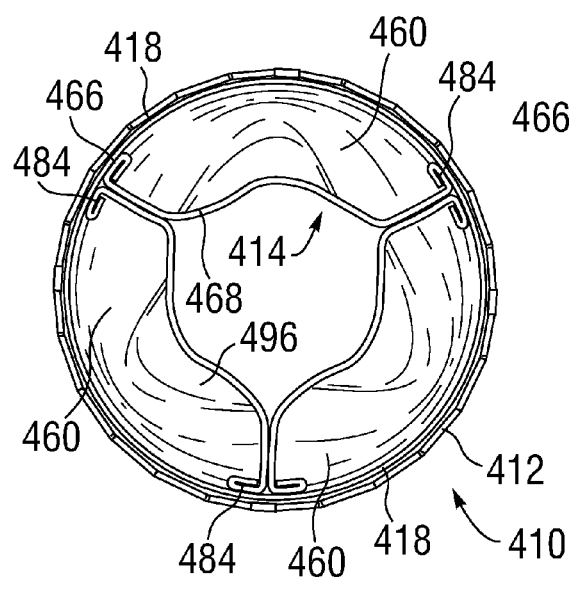
FIG. 32 is a top view of an exemplary valve formed by turning the sleeve of FIG. 31 inside-out and suturing it within an exemplary frame.
Figure 33:
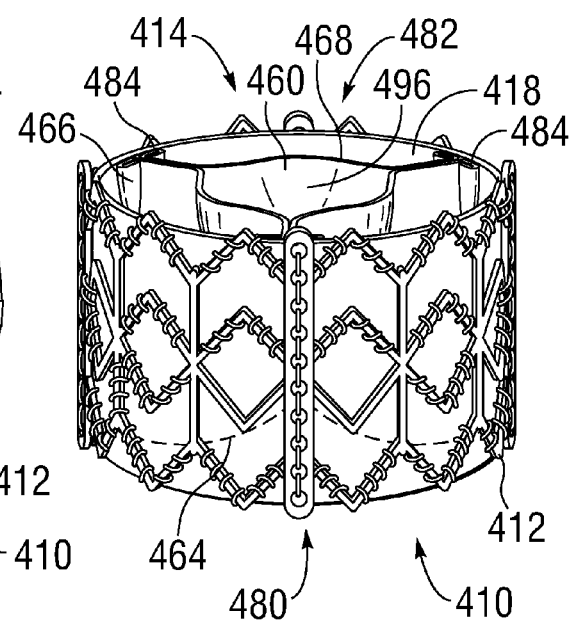
FIG. 33 is a perspective view of the valve of FIG. 32.

The inner structure 414 can then be positioned within the frame 412 and the sleeve 418 can be sewn to the interior surface of the frame to form the valve 410, as shown in FIG. 32. The valve 410 has an inflow end 480 adjacent to the curved lower edges 464 of the leaflets and an outflow end 482 adjacent to the upper edges 468 of the leaflets. An upper end portion 422 and a lower end portion 424 of the sleeve 418 (see FIG. 31) can be trimmed to match the dimensions of the frame 412. In FIG. 33, the sleeve 418 extends the full axial height of the frame 412. Because the leaflets 460 are secured to the sleeve 418, the frame 412 need not include commissure attachment posts (although the frame 412 shown in FIG. 33 does include them) that align with commissures 484 of the inner structure 414. The sleeve 418 can be sewn to the frame 412 around the whole circumference of the valve 410, not just at the commissures 484, as shown in FIG. 33. The sleeve 418 can act as a scaffold to support the leaflets 460 and can replace the functions of a skirt, as described above.

The inner structure 414 is adaptable to be sewn within a variety of different frame types. The sleeve 418 can be trimmed to any length and/or pattern and any portion of the sleeve can be attached to a frame. This versatility can allow, for example, a tricuspid leaflet structure to be secured with a frame having four commissure posts, as shown in FIGS. 32 and 33.

This modular construction process can allow for the inner structure 414 to be manufactured in a different control environment from the frame 412. For example, tissue components may require a more controlled manufacturing environment than metal components. In addition, the final assembly of the inner structure 414 to the frame 412 can be performed in a differently controlled environment.

In view of the many possible embodiments to which the principles disclosed herein may be applied, it should be recognized that the illustrated embodiments are only preferred examples and should not be taken as limiting the scope of the disclosure. Rather, the scope is defined by the following claims. We therefore claim all that comes within the scope and spirit of these claims.

We claim:
1. An implantable prosthetic valve, comprising:
a radially collapsible and expandable annular frame;
an annular skirt coupled to an inner side of the frame;
a leaflet structure positioned within the frame and the annular skirt and comprising a plurality of leaflets each comprising two opposing side tabs, wherein each leaflet comprises a separate piece of material, wherein each side tab is rolled into a spiral and each spiral is positioned next to an adjacent spiral of an adjacent leaflet to form a plurality of annularly spaced commissures of the leaflet structure, and wherein each spiral is coupled to the annular skirt;

wherein the side tab of each spiral is rolled around a central longitudinal axis of the spiral greater than 360 degrees such that at least two layers of the side tab are in contact with each other;

wherein the skirt comprises a single sheet of material that extends continuously around the leaflet structure, and each leaflet has an inflow end portion that is sutured to the skirt by a suture line that extends along the inflow end portion of each leaflet.

2. The valve of claim 1, wherein each spiral comprises a non-rigid reinforcing material that reinforces the spirals to resist suture tear-through.

3. The valve of claim 2, wherein the reinforcing material comprises a plurality of inserts, at least one insert being positioned within each spiral.

4. The valve of claim 3, wherein for each spiral, at least one suture intersects at least three layers of the respective side tab and the at least one insert within the spiral.

5. The valve of claim 3, wherein for each spiral, stitches of at least one suture intersect at least: a first two layers of the spiral, an insert within the spiral, a second two layers of the spiral, and the skirt, in that order.

6. The valve of claim 3, wherein the inserts are tubular and comprise a compressible material and are retained in a compressed state by sutures extending radially through the spirals.

7. The valve of claim 3, wherein each spiral is sutured to the skirt with a respective suture that intersects the spiral, the reinforcing insert, and the skirt.

8. The valve of claim 1, wherein for each spiral, at least one suture intersects at least four different layers of the respective side tab.

9. The valve of claim 1, wherein for each spiral, at least one suture extending in a generally radial direction secures the spiral to the skirt.

10. The valve of claim 1, wherein each spiral provides a curved, cushioned surface for a flex hinge portion of the respective leaflet to bear against as the leaflet articulates between an open and a closed position.

11. The valve of claim 1, wherein each leaflet comprises an articulation portion extending between the two spirals of each leaflet and the spirals provide a radial clearance between the frame and articulation portions of the leaflets.

12. The valve of claim 1, wherein each leaflet comprises an articulation portion extending between the two spirals of each leaflet, and the two spirals of each commissure are secured to the skirt with sutures spaced away from the articulation portions of the leaflets.

13. The valve of claim 1, wherein the leaflets comprise bovine pericardium tissue harvested from one or more calves less than about four weeks of age.

14. The valve of claim 13, wherein the tissue is harvested from calves between about one week and about two weeks of age.

15. The valve of claim 1, wherein the two spirals of each commissure are not sutured together.

16. An implantable prosthetic valve, comprising:
a radially collapsible and expandable annular frame; and
a leaflet structure positioned within the frame and comprising a plurality of leaflets each comprising two opposing side tabs, wherein each leaflet comprises a separate piece of material, wherein each side tab is rolled into a spiral and each spiral is positioned next to an adjacent spiral of an adjacent leaflet to form a plurality of annularly spaced commissures of the leaflet structure;

wherein the side tab of each spiral is rolled around a central longitudinal axis of the spiral greater than 360 degrees such that at least two layers of the side tab are in contact with each other.

17. The valve of claim 16, wherein the two spirals of each commissure are not sutured together.

18. The valve of claim 17, wherein the two spirals of each commissure are sutured radially outwardly to an annular skirt such that the two spirals of each commissure are held against each other.

19. The valve of claim 16, wherein each spiral comprises a non-rigid reinforcing material that reinforces the spirals to resist suture tear-through.

* * * * *